US012611219B2

(12) United States Patent
Wang et al.

(10) Patent No.: US 12,611,219 B2
(45) Date of Patent: Apr. 28, 2026

(54) ELECTRODE ASSEMBLY AND SHOCK WAVE APPARATUS USING THE ELECTRODE ASSEMBLY

(71) Applicant: PEIJIA MEDICAL (SUZHOU) CO., LTD., Suzhou (CN)

(72) Inventors: Jian'an Wang, Suzhou (CN); Xianbao Liu, Suzhou (CN); Shangshang Ding, Suzhou (CN); Yuhu Cui, Suzhou (CN); Jian Fong Tan, Suzhou (CN); Yi Zhang, Suzhou (CN)

(73) Assignee: Peijia Medical (Suzhou) Co., Ltd., Jiangsu (CN)

( * ) Notice: Subject to any disclaimer, the term of this patent is extended or adjusted under 35 U.S.C. 154(b) by 261 days.

(21) Appl. No.: 18/366,345

(22) Filed: Aug. 7, 2023

(65) Prior Publication Data

US 2023/0389947 A1 Dec. 7, 2023

Related U.S. Application Data

(63) Continuation-in-part of application No. PCT/CN2022/074972, filed on Jan. 29, 2022, and a
(Continued)

(30) Foreign Application Priority Data

Feb. 5, 2021 (CN) .......................... 202110164455.7
Feb. 5, 2021 (CN) .......................... 202110164461.2

(51) Int. Cl.
*A61B 17/22* (2006.01)
*A61B 17/00* (2006.01)

(52) U.S. Cl.
CPC ................... *A61B 17/22022* (2013.01); *A61B 2017/00243* (2013.01); *A61B 2017/22025* (2013.01);
(Continued)

(58) Field of Classification Search
CPC .......... A61B 17/22012; A61B 17/2202; A61B 17/22022; A61B 2017/22029;
(Continued)

(56) References Cited

U.S. PATENT DOCUMENTS 6,935,702 B2 8/2005 Okazaki et al.
10,786,267 B2 9/2020 WasDyke et al.
(Continued)

FOREIGN PATENT DOCUMENTS

CN 1461239 A 12/2003
CN 203564304 U 4/2014
(Continued)

*Primary Examiner* — Kathleen S Holwerda
(74) *Attorney, Agent, or Firm* — Grogan, Tuccillo & Vanderleeden, LLP

(57) ABSTRACT

An electrode assembly for a shock wave apparatus. An electrode assembly (30) is disposed inside a balloon (10) of a shock wave apparatus (100). The electrode assembly (30) comprises: a first electrode (301); an insulating layer (302), the first electrode (301) being disposed inside the insulating layer (302) and the tail end of the first electrode (301) being exposed from the tail end of the insulating layer (302); a first electrical conductor (303), the first electrical conductor (303) being disposed on at least a portion of the outer peripheral surface of the tail end of the insulating layer (302); and a second electrode (304), the second electrode (304) being disposed on at least a portion of the outer peripheral surface of a base end of the insulating layer (302), such that an insulating gap is provided between the second electrode (304) and the first electrical conductor (303).

17 Claims, 10 Drawing Sheets

Related U.S. Application Data continuation-in-part of application No. PCT/CN2022/074971, filed on Jan. 29, 2022.

(52) U.S. Cl.
CPC ............... *A61B 2017/22062* (2013.01); *A61B 2017/22098* (2013.01)

(58) Field of Classification Search
CPC  A61B 2017/22021; A61B 2017/22025; A61B 2017/22062; A61B 2017/22098
See application file for complete search history.

(56) References Cited

U.S. PATENT DOCUMENTS

| | | | |
|---|---|---|---|
| 2009/0312768 A1 | 12/2009 | Hawkins et al. | |
| 2011/0034832 A1* | 2/2011 | Cioanta ............ | A61B 17/22004 601/1 |
| 2013/0030431 A1* | 1/2013 | Adams ............. | A61B 17/22022 606/41 |
| 2014/0039513 A1 | 2/2014 | Hakala et al. | |
| 2016/0135828 A1 | 5/2016 | Hawkins et al. | |
| 2017/0135709 A1 | 5/2017 | Nguyen et al. | |
| 2018/0360482 A1* | 12/2018 | Nguyen .......... | A61B 17/22022 |
| 2019/0029703 A1* | 1/2019 | Wasdyke ......... | A61B 17/22022 |
| 2020/0129196 A1* | 4/2020 | McCaffrey ....... | A61B 17/22022 |
| 2022/0287731 A1 | 9/2022 | Tany et al. | |

FOREIGN PATENT DOCUMENTS

| | | |
|---|---|---|
| CN | 104582621 A | 4/2015 |
| CN | 109303586 A | 2/2019 |
| CN | 110604607 A | 12/2019 |
| CN | 110811761 A | 2/2020 |
| CN | 111790046 A | 10/2020 |
| CN | 114869400 A | 8/2022 |
| EP | 3522797 B1 | 11/2020 |
| JP | 2003001135 A | 1/2003 |
| JP | 2004181423 A | 7/2004 |

* cited by examiner

ELECTRODE ASSEMBLY AND SHOCK WAVE APPARATUS USING THE ELECTRODE ASSEMBLY

CROSS-REFERENCE TO RELATED APPLICATIONS

The present application is a continuation-in-part of both International Application No. PCT/CN2022/074971, filed on Jan. 29, 2022, which claims the benefit of priority to Chinese Application No. 202110164455.7, filed on Feb. 5, 2021, and International Application No. PCT/CN2022/074972, filed on Jan. 29, 2022, which claims the benefit of priority to Chinese Application No. 202110164461.2, filed on Feb. 5, 2021, the entire disclosures of which are all expressly incorporated by reference herein in their entireties and the priorities of which are all claimed by the present application.

TECHNICAL FIELD

The present disclosure belongs to the technical field of medical techniques, in particular, to an electrode assembly used in a shock wave apparatus for treating cardiac valve or blood vessel calcification, a shock wave apparatus using the electrode assembly, and a method for treating cardiac valve or blood vessel calcification of an animal.

BACKGROUND

Cardiac valve calcification is a main pathological manifestation of stenosis and regurgitation of a cardiac valve, etc., and usually taken place in elderly people. Blood vessel calcification is a generally common pathological manifestation of atherosclerosis, hypertension, diabetic vasculopathy, a vessel injury, a chronic renal disease and decrepitude, etc.

At present, a shock wave balloon technique has been used for treating cardiac valve or blood vessel calcification due to existence the advantages of being easily operated and performing pre-dilation by a balloon. As shown in FIG. 1, a shock wave apparatus 900 for treating cardiac valve calcification in the prior art includes a shock wave transmitter 920 and a balloon 910. The shock wave transmitter 920 comprises electrode cables which receive and conduct a voltage/current pulse and an electrode assembly 922 which is electrically connected to the electrode cables and is used for receiving the voltage/current pulse to generate shock wave. The balloon 910 is wrapped around the shock wave transmitter 920 from outside, and has stretchable, foldable and insulative properties. The balloon 910 is also provided with a through hole for the inflow of fluids, so that interior of the balloon 910 is filled with the fluid. The balloon 910 is dilated when the interior of the balloon 910 is filled with the fluid, so that at least a portion of outer surfaces of the balloon 910 comes into contact with a cardiac valve or blood vessel at which a calcification lesion is present (hereinafter sometimes abbreviated as "a calcification lesion portion" or "a cardiac valve or blood vessel having a calcification lesion"). The shock wave generated by the electrode assembly 922 is radially conducted to a surface of the balloon 910 through the liquid inside the balloon 910, and is then conducted to the calcification lesion portion through the surface of the balloon. When the shock wave is conducted to the calcification lesion portion, a compressive stress of the shock wave causes a fracture of calcified tissue at the calcification lesion portion. A shock wave of an appropriate intensity can achieve of breaking the calcified tissue without causing an additional burden of soft tissue around the calcified tissue.

However, the electrode assembly of the shock wave apparatus in the existing technique is mainly formed by a metal conductor and an insulating sheath; and higher energy is always required for the treatment of a cardiac valve calcification lesion, thus a voltage between a positive electrode and a negative electrode of a shock wave electrode may reach 7 KV to 10 KV, and the electrode generates intense thermal energy and mechanical energy during discharging, which causes a destructive impact to the structure of the shock wave electrode, bringing about great challenges to the service life of the shock wave electrode. In addition, in the case of severe cardiac valve or blood vessel calcification, it always leading to that it's difficult for the balloon of the shock wave apparatus to smoothly enter into the calcification lesion portion. Therefore, there are requirements for improvement in terms of the improving the treatment accuracy and effectiveness for the calcification lesion portion, the prolonging of the service life of the shock wave electrode in a high-voltage state, an optimized design of an electrode control system, etc.

In addition, a method of multi-channel control at low-voltage circuits is used in the shock wave apparatus that is provided with the plurality of balloons and/or the plurality of shock wave transmitters in the related art. In the control method, a multiple-channels control circuit is arranged ahead of a boost circuit, and each circuit needs a separate boost circuit and a separate high-voltage trigger switch. Since the volume of a boost component and the high-voltage trigger switch are relatively large, the overall circuit volume is relatively large, which results in a relatively large volume of the shock wave apparatus, thus causing the problem of inconvenient operation during an interventional surgery.

SUMMARY

In view of the described technical problems in the related art, the present disclosure provides an electrode assembly which is used in a shock wave apparatus for treating cardiac valve or blood vessel calcification and by which the attenuation of a shock wave during conduction can be effectively reduced, and a satisfactory therapeutic effect is achieved for the cardiac valve or blood vessel calcification. In addition, by means of the electrode assembly of the present disclosure, the service life of an electrode and the shock wave apparatus can be significantly prolonged. The electrode assembly of the present disclosure can also enable the shock wave apparatus to quickly enter into a calcification lesion portion of a cardiac valve, thereby effectively shortening the time for a surgery. In addition, the present disclosure further provides a shock wave apparatus using the electrode assembly of the present disclosure, a control system for controlling the shock wave apparatus of the present disclosure, and a method for treating cardiac valve or blood vessel calcification using the shock wave apparatus of the present disclosure.

To solve the described technical problems, one aspect of embodiments of the present disclosure provides an electrode assembly for a shock wave apparatus which is disposed inside a balloon of the shock wave apparatus, and the electrode assembly includes:

a first electrode;

an insulating layer, the first electrode being disposed
inside the insulating layer and a terminal end of the first
electrode being exposed from a terminal end of the
insulating layer;

a first electrical conductor disposed on at least a portion
of an outer peripheral surface of the terminal end of the
insulating layer; and a second electrode disposed on at least a portion of an
outer peripheral surface of a base end of the insulating
layer, such that an insulating gap is provided between
the second electrode and the first electrical conductor.

According to the electrode assembly of one aspect of the
embodiments of the present disclosure, at least one of the
first electrical conductor and the second electrode is pro-
vided with a protruding part which extends from one of the
first electrical conductor and the second electrode to the
other of the first electrical conductor and the second elec-
trode along an outer peripheral surface of the insulating
layer.

According to the electrode assembly in one aspect of the
embodiments of the present disclosure, the electrode assem-
bly further includes at least one second electrical conductor
which is disposed on at least a portion of the outer peripheral
surface of the insulating layer and is located between the first
electrical conductor and the second electrode, such that an
insulating gap is provided between the first electrical con-
ductor and the second electrical conductor and between the
second electrical conductor and the second electrode.

According to the electrode assembly in one aspect of the
embodiments of the present disclosure, the at least one
second electrical conductor is provided with a protruding
part which extends from the second electrical conductor to
the base end or the terminal end of the insulating layer along
the outer peripheral surface of the insulating layer.

According to the electrode assembly in one aspect of the
embodiments of the present disclosure, the first electrical
conductor, the second electrical conductor and the second
electrode are provided with two or more protruding parts in
total, the two or more protruding parts are spaced apart from
one another in a circumferential direction of the insulating
layer by an angle of $\alpha$, $\alpha=360°/N$, and N is the number of
the protruding parts.

According to the electrode assembly in one aspect of the
embodiments of the present disclosure, the first electrode
can be moved inside the insulating layer in an axial direc-
tion, and the terminal end of the first electrode is provided
with a connecting part which makes the first electrode
electrically connecting or electrically disconnecting the first
electrical conductor during the movement of the first elec-
trode.

According to the electrode assembly in one aspect of the
embodiments of the present disclosure, the first electrode is
a rod-shaped electrode having a diameter of 0.1 mm to 1.0
mm, preferably 0.1 mm to 0.5 mm.

According to the electrode assembly in one aspect of the
embodiments of the present disclosure, the second electrode
is an annular electrode having a wall thickness of 0.1 mm to
1.0 mm.

According to the electrode assembly in one aspect of the
embodiments of the present disclosure, each of the first
electrical conductor and the second electrical conductor is an
annular electrical conductor having a wall thickness of 0.1
mm to 1.0 mm.

According to the electrode assembly in one aspect of the
embodiments of the present disclosure, the insulating layer
is a cylindrical insulating sheath having a wall thickness of
0.1 mm to 1.0 mm.

According to the electrode assembly in one aspect of the
embodiments of the present disclosure, the electrode assem-
bly further comprises a second insulating layer, the second
insulating layer being disposed inside the insulating layer,
and the first electrode being disposed on at least a portion of
an outer peripheral surface of a terminal end of the second
insulating layer.

According to the electrode assembly in one aspect of the
embodiments of the present disclosure, the electrode assem-
bly comprises two or more second electrical conductors with
an insulating gap provided between any two adjacent second
electrical conductors.

According to the electrode assembly in one aspect of the
embodiments of the present disclosure, the electrode assem-
bly comprises two to five second electrical conductors.

According to the electrode assembly in one aspect of the
embodiments of the present disclosure, the first electrode is
an annular electrode having a wall thickness of 0.05 mm to
0.2 mm, and the second electrode is an annular electrode
having a wall thickness of 0.05 mm to 0.2 mm.

According to the electrode assembly in one aspect of the
embodiments of the present disclosure, the first electrical
conductor is an annular electrical conductor having a wall
thickness of 0.05 mm to 0.2 mm.

According to the electrode assembly in one aspect of the
embodiments of the present disclosure, the second insulating
layer is a cylindrical insulating layer having an inner diam-
eter of 0.3 mm to 0.4 mm and a wall thickness of 0.1 mm
to 0.2 mm.

Another aspect of the embodiments of the present disclo-
sure provides a shock wave apparatus including the above-
mentioned electrode assembly of the present disclosure.

Another aspect of the embodiments of the present disclo-
sure provides a shock wave apparatus, the shock wave
apparatus includes two or more balloons, and at least one
balloon of the two or more balloons is internally provided
with the above-mentioned electrode assembly of the present
disclosure.

Still another aspect of the embodiments of the present
disclosure provides a method for treating cardiac valve
calcification, the method uses the above-mentioned shock
wave apparatus of the present disclosure to treat a calcified
portion of a cardiac valve.

Still further another aspect of the embodiments of the
present disclosure provides a method for treating blood
vessel wall calcification, the method uses a shock wave
apparatus comprising the above-mentioned electrode assem-
bly to treat a calcified portion of a blood vessel.

According to one embodiment of the present disclosure,
an electrode assembly used in a shock wave apparatus for
treating cardiac valve or blood vessel calcification can be
provided. The electrode assembly can not only effectively
reduce the attenuation of a shock wave during conduction,
but also prolong the service life of the electrode assembly,
thereby achieving a satisfactory therapeutic effect safely and
reliably. In addition, the shock wave apparatus of the present
disclosure is easily operated, and the requirement for the
degree of operation proficiency of an operator is signifi-
cantly reduced, such that the time for a surgery can be
significantly shortened, and a burden of a treatment subject
is alleviated, thereby improving the success rate of the
surgery, and effectively avoiding various types of risks
during the surgery.

BRIEF DESCRIPTION OF THE DRAWINGS

In order to more clearly illustrate the technical solutions
in the embodiments of the present disclosure, the drawings used in the description of the exemplary embodiments will be briefly described below. Obviously, the drawings in the following description are only some embodiments of the present disclosure, and an ordinary skilled technician in the art can obtain other drawings according to the drawings without involving any inventive effort.

DETAILED DESCRIPTION

The technical solutions in the embodiments of the present disclosure will be clearly and completely described below in conjunction with the drawings in the embodiments of the present disclosure. Apparently, the embodiments described are only some rather than all of the embodiments of the present disclosure. All other embodiments obtained by an ordinary skilled technician in the art based on the embodiments of the present disclosure without involving any inventive effort all fall within the scope of protection of the present disclosure.

In the present application, "shock wave" is a general term for various forms of waves (e.g. a pressure wave) that can be generated by an electrode assembly during charging, and is not used to define the specific form of wave.

In the present application, a "distal end" or a "terminal end" of a component of the shock wave apparatus or the electrode assembly or the like refers to an end that is a lead head end which enters into the body of a treatment subject during a surgery, and a "proximal end" or a "base end" of the shock wave apparatus or a component thereof is the end closer to a handle which is left outside of the body of the treatment body during the surgery compared to the "far end" and "end end".

In the present application, "a plurality of" refers to two or more. In view of this, "a plurality of" can be understood as "at least two" in the embodiments of the present disclosure. The term of "and/or" describes an association relationship between associated objects and represents that there may be three relationships. For example, A and/or B may represent: only A exists, both A and B exist, and only B exists. In addition, unless otherwise specified, the character of "/" generally indicates that the associated objects before and after the character are in an "or" relationship.

In the present application, "cardiac valve" and "valve" is a general term for valves including a mitral valve, a tricuspid valve and an aortic valve. In the present application, "a cardiac valve or blood vessel at which a calcification lesion is present" refers to "a cardiac valve and a blood vessel having a calcification lesion" or "a calcification lesion portion".

Shock Wave Apparatus

Figures 1, 2, 3:
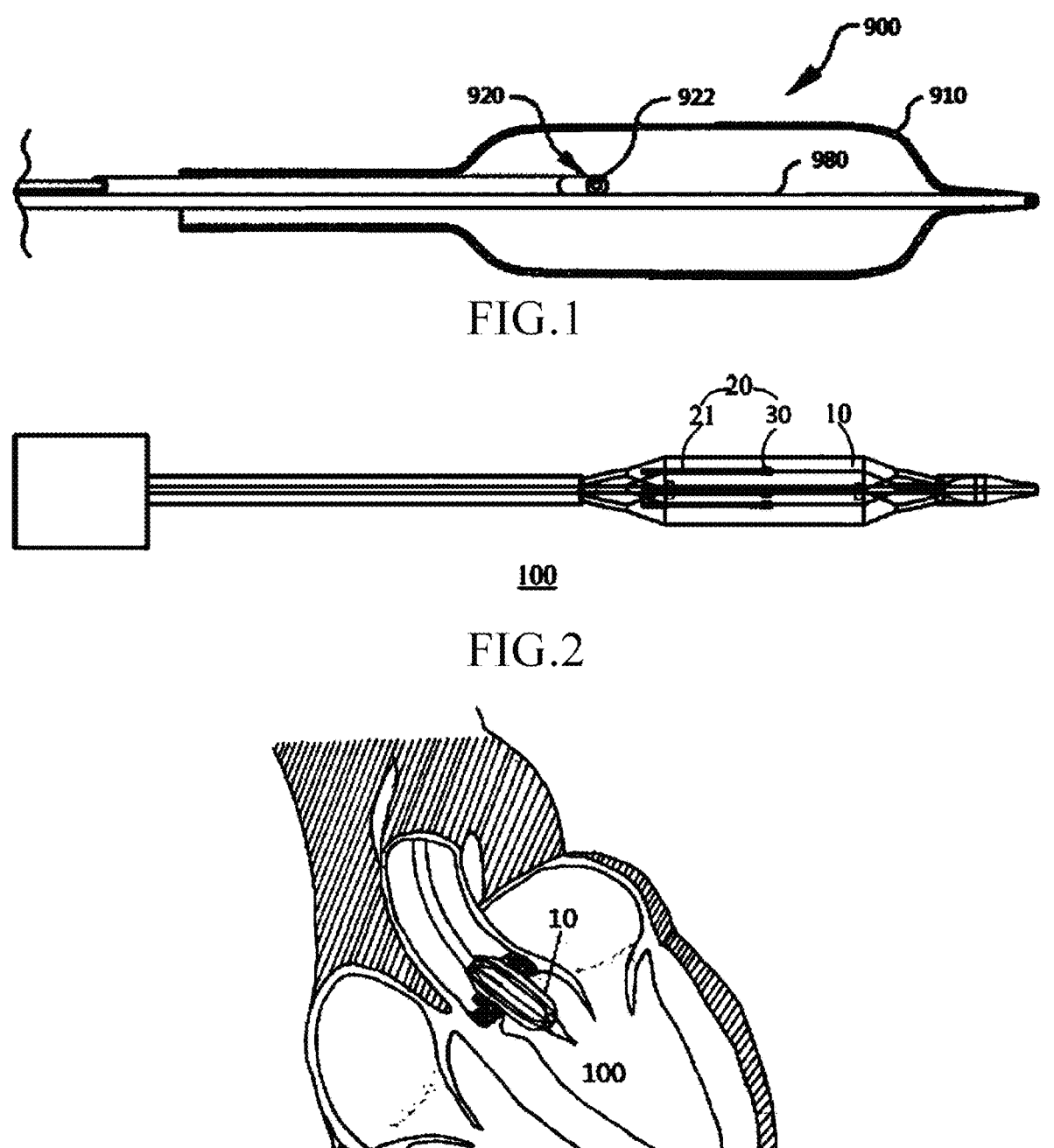
FIG. 1 shows the structure of a shock wave apparatus in the prior art.
FIG. 2 shows the structure of one exemplary embodiment of a shock wave apparatus of the present disclosure.
FIG. 3 shows the usage state of one exemplary embodiment of the shock wave apparatus of the present disclosure.

As shown in FIG. 2, the shock wave apparatus 100 of one exemplary embodiment of the present disclosure may comprise at least one balloon 10. The balloon 10 is provided with at least one balloon body. Preferably, the balloon body of the balloon 10 is cylindrical after dilated. The shapes of two end parts of each balloon in a lengthwise direction are not specifically defined as long as the dilated balloon body of the balloon 10 is cylindrical. More preferably, the cylindrical balloon bodies of the balloon 10 are parallel to each other in the lengthwise direction. Specifically, axes of the cylindrical balloon bodies of the balloon 10 in the respective lengthwise directions are parallel to each other. The balloon 10 of the shock wave apparatus of the present disclosure may also have other shapes. For example, in one embodiment of the present disclosure, the balloon 10 may be provided with a plurality of balloon bodies. These balloon bodies may have the same shape, for example, a cylinder shape after being dilated with a liquid, and these balloon bodies are in communication with each other, such that the liquid can flow among these balloon bodies.

The balloon 10 may be formed from polymer materials as semi-compliance or non-compliance balloon with stretchable, foldable and insulative properties. The material forming the balloon 10 is not specifically limited, and may be, for example, nylon, polyether block amide (PEBA) or polyethylene terephthalate (PET), etc. The balloon 10 is also provided with at least one through hole which are in communication with a connecting tube A14 and is used for injecting liquid into the balloon 10 so that the balloon 10 is dilated. After the interior of the balloon 10 is filled with the fluid, the balloon is dilated, such that at least a portion of an outer surface of the balloon 10 comes into contact with a cardiac valve or blood vessel having a calcification lesion (a calcification lesion portion).

The balloon 10 is internally disposed with at least one shock wave transmitter 20 which is used for receiving a voltage/current pulse and generating shock wave. Preferably, as shown in FIG. 2, each balloon body of the balloon 10 is internally disposed with at least one shock wave transmitter 20. The shock wave transmitter 20 comprises at least one an electrode cable 21 which receives and conducts a voltage/current pulse and at least one electrode assembly 30 which is electrically connected to the electrode cable 21 and is used for receiving the voltage/current pulse to generate a shock wave. The shock wave generated by the electrode assembly 30 is radially conducted to a surface of the balloon 10 through the liquid inside the balloon 10, and is then conducted to a calcification lesion portion through the surface of the balloon.

As shown in FIG. 3, during a surgery, the balloon 10 of the shock wave apparatus 100 is positioned at a cardiac valve position, for example. Preferably, the position of the electrode assembly 30 inside the balloon 10 corresponds to the calcification lesion portion, such that the distance between the electrode assembly 30 and the calcification lesion portion is the shortest.

Figure 4:
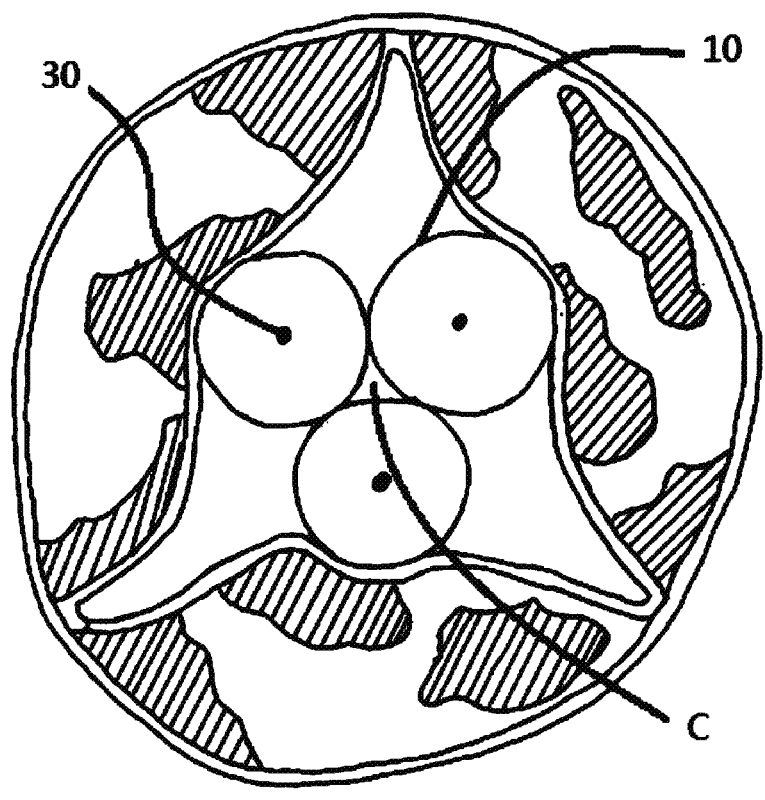
FIG. 4 is a schematic cross-sectional diagram of a balloon portion of the shock wave apparatus of the present disclosure in an operation state.

FIG. 4 shows a schematic cross-sectional diagram of a balloon portion of the shock wave apparatus 100 shown in FIG. 3 in operation state (dilated). As shown in FIG. 4, each balloon 10 includes a shock wave transmitter 20 which is disposed inside the balloon body of the balloon. Therefore, compared with the shock wave apparatus 900 in the prior art shown in FIG. 1, when the shock wave apparatus 100 of one exemplary embodiment of the present disclosure is in operation state, the distance between the electrode assembly 30 of the shock wave transmitter 20 that generates shock wave and a portion of the outer surface of the balloon 10 that is in contact with the calcification lesion portion is significantly shortened. Therefore, a shock wave generated by a lower voltage/current pulse can maintain sufficient intensity even though the shock wave is conducted to the calcification lesion portion, thereby obtaining a satisfactory therapeutic effect.

In another aspect, since the shock wave apparatus 100 of the present disclosure have a structure described above, that is, the cylindrical balloon bodies of each balloon 10 in the shock wave apparatus 100 are parallel to each other, the balloons are not prone to displacement caused by the slight pressing of a valve when the balloons are in contact with the calcification lesion portion during a surgery, and therefore, a healthcare worker can obtain a satisfactory therapeutic effect only by performing simple positioning operations. The requirement to operation proficiency level of the operator by the shock wave apparatus 100 in the embodiments of the present disclosure is significantly reduced, such that an operator having ordinary intervention surgery experience can proficiently operate the shock wave apparatus 100 of the present disclosure. Therefore, the time for a surgery can be significantly shortened, and a burden to a treatment subject is alleviated, thereby improving the success rate of the surgery, and reducing various types of risks during the surgery.

In another aspect, in one embodiment of the present disclosure, a plurality of balloons 10 are provided, and a gap for passage of blood is provided between or among balloons 10, such that a surgery can be performed in a case of ensuring the blood to flow without blocking, thereby alleviating a burden to a treatment subject caused by the surgery. Specifically, as shown in FIG. 4, after the plurality of balloons 10 (three in the figure) are dilated, an adequate gap is reserved in both a balloon outer-side region and a balloon inner-side region (portion C in FIG. 4). In an exemplary embodiment of the present disclosure as shown in FIG. 4, the shock wave apparatus 100 is provided with three balloons 10. However, in the other embodiments of the present disclosure, there may be two, four or more balloons 10.

In the shock wave apparatus 100 of an exemplary embodiment of the present disclosure, the diameter of a body portion of a balloon 10 is 2 mm to 12 mm. The diameter of the balloon 10 is preferably 6 mm to 10 mm, and more preferably 8 mm to 10 mm. When the diameter of the balloon is greater than 12 mm, the distance between the electrode assembly and the calcification lesion portion increases, posing a risk of over-attenuation of the intensity of shock wave.

The length of the body portion of the balloon 10 is 20 mm to 60 mm, for example, 20 mm, 35 mm, mm, 55 mm or 60 mm. When the balloon 10 is excessively long, there is a possibility of damage to heart tissue during the surgery, and it is too difficult for the shock wave apparatus to pass a bend when being delivered during the intervention surgery. On the other hand, when the balloon 10 is excessively short, it will be more difficult for operator to position the shock wave apparatus during the surgery.

The fluid which is used in the shock wave apparatus 100 and is injected into the balloon 10 is not specifically limited. The liquid may be an electrolyte liquid, for example, normal saline, etc., or the liquid may also be a non-electrolyte liquid, for example, glycerinum, etc.

The balloon 10 of the shock wave apparatus 100 of the present disclosure may be designed as a disposable consumable or a consumable that can be repeatedly used. When the balloon is the consumable that can be repeatedly used, disinfection and sterilization are required before using it. Moreover, the shock wave apparatus 100 of the present disclosure is provided with a plurality of separate balloons 10, and therefore, when one balloon is broken, it is possible to replace the broken balloon only, instead of discarding the entire shock wave apparatus, thereby significantly reducing the cost of a maintenance fee of the shock wave apparatus.

Electrode Assembly 30

Figure 5:
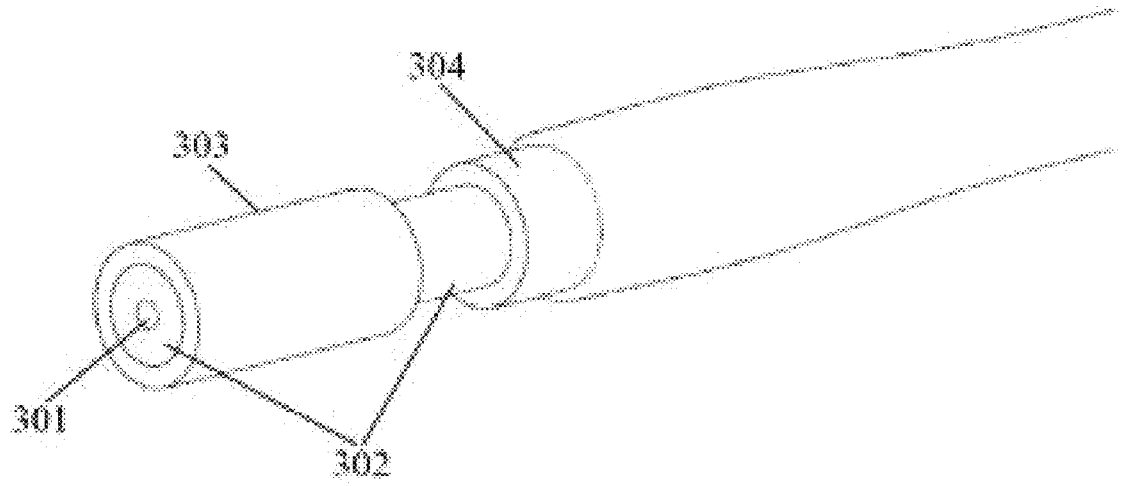
FIG. 5 is a schematic diagram of an exemplary embodiment of an electrode assembly for a shock wave apparatus of the present disclosure.

FIG. 5 shows an exemplary example of the electrode assembly of the present disclosure. As shown in FIG. 5, in one exemplary embodiment of the present disclosure, the electrode assembly 30 comprises an inner electrode 301, an insulating layer 302, a first electrical conductor 303 and an outer electrode 304.

The inner electrode 301 is a first electrode, which is disposed on the innermost layer of the electrode assembly 30, and is electrically connected to a power supply unit by means of a wire of the electrode cable 21. The material forming the inner electrode 301 is not specifically limited, may be any electrical conductor, but is preferably metal materials such as copper, silver, tungsten, etc. The shape of the inner electrode 201 is not specifically limited. However, as shown in FIG. 5, the inner electrode preferably has a rod shape with a circular cross section. The diameter of the rod-shaped inner electrode 301 is 0.1 mm to 1.0 mm, and preferably 0.1 mm to 0.5 mm.

The insulating layer 302 covers at least a portion of an outer peripheral surface of the inner electrode 301, such that a terminal end of the inner electrode 301 is exposed from a terminal end of the insulating layer 302. The terminal end of the inner electrode 301 may also be aligned with the terminal end of the insulating layer 302, alternatively, the terminal end of the inner electrode 301 may protrude from the terminal end of the outer insulating layer 302. The material forming the insulating layer 302 is not specifically limited and may be any insulator, but is preferably high-voltage resistant material such as polyimide or polytetrafluoroethylene. The shape of the insulating layer 302 is not specifically limited, as shown in FIG. 5, while is preferably an insulating sheath that covers the outer peripheral surface of the inner electrode 301 and has an annular cross section. The wall thickness of the annular insulating sheath is 0.1 mm to 1.0 mm, and preferably 0.2 mm to 0.5 mm. The length of the inner electrode 301 that is exposed from the distal end of the insulating layer 302 is not specifically defined.

The first electrical conductor 303 is disposed at the terminal end of the insulating layer 302 and covers at least a portion of the outer peripheral surface of the insulating layer 302. The first electrical conductor is not electrically connected to the power supply unit, and thus does not have any polarity. The material for forming the first electrical conductor 303 is not specifically limited, may be any conductor, but is preferably metal materials such as stainless steel, copper, etc. The shape of the first electrical conductor 303 is not specifically limited. However, as shown in FIG. 5, the first electrical conductor preferably has an annular shape that covers the outer peripheral surface of the terminal end of the insulating layer 302. The wall thickness of the annular first electrical conductor 303 is 0.1 mm to 1.0 mm.

Compared to the first electrical conductor 303, the outer electrode 304 is disposed at the base end of the insulating layer 302 spaced apart from the first electrical conductor 303 by a certain distance, and covers at least a portion of the outer peripheral surface of the insulating layer 302. The outer electrode 304 is a second electrode, which is electrically connected to the power supply unit by means of one wire of the electrode cable 21. The material for forming the outer electrode 304 is not specifically limited, but is preferably metal materials such as stainless steel, copper, etc. The shape of the outer electrode 304 is not specifically limited, as shown in FIG. 5, while preferably has an annular shape that covers the outer peripheral surface of the base end of the insulating layer 302. The wall thickness of the annular outer electrode 304 is 0.1 mm to 1.0 mm. As shown in FIG. 5, an insulating gap is provided between the first electrical conductor 303 and the outer electrode 304 which are disposed on the outer peripheral surface of the insulating layer 302.

Based on the described electrode assembly 30, when a voltage is applied between the inner electrode 301 and the outer electrode 304, due to a voltage difference formed between the inner electrode 301 and the outer electrode 304 and according to voltage dividing principle in series circuits, voltage differences also exist in a gap (a first discharge point) between the terminal end of the inner electrode 301 and the first electrical conductor 303 and in a gap (a second discharge point) between the first electrical conductor 303 and the outer electrode 304. Mediums at the first discharge point and the second discharge point are broken down at the same time and shock wave energy is generated due to the presence of above voltage differences. Shock wave energy generated at the first discharge point (a head end of the electrode assembly 30) is radially conducted in an axial direction of the electrode assembly 30, while shock wave energy generated at the second discharge point is radially conducted in a radial direction of the electrode assembly 30.

Satisfactory effects can be obtained when the manner of discharge and shock wave conduction described above is used for treating severer cardiac valve and blood vessel calcification, especially severe cardiac valve calcification. When severe calcification occurs at, for example, a cardiac valve, it is difficult for the balloon of the shock wave apparatus to enter into a valvular annulus to dilate the valve. Therefore, when the shock wave apparatus which is provided with the electrode assembly 30 of the present disclosure is used, the shock wave which is generated at the first discharge point is conducted forward in the axial direction of the electrode assembly 30, so as to perform shock wave pre-dilation on a severely calcified valve, such that the balloon easily enters the valvular annulus. When the balloon of the shock wave apparatus completely enters into the valvular annulus, the shock wave which is generated at the second discharge point and is conducted in a radial direction of the electrode assembly 30 can further act on the calcification lesion portion. Therefore, more satisfactory effects can be obtained when the electrode assembly 30 of the present disclosure is used to treat a treatment subject having severe cardiac valve calcification, for example.

In an exemplary example of electrode assembly 30 shown in FIG. 5, a discharge gap (a discharge distance) $D_1$ at the first discharge point is constant, and $D_1$ is approximately the wall thickness of the insulating layer 302. A discharge gap $D_2$ at the second discharge point is not specifically limited. However, the sum of $D_1$ and $D_2$, i.e., the total discharge gap $D$ ($D=D_1+D_2$) should be smaller than the maximum distance $D_{max}$ that can be broken down by an actual operation voltage. For example, taking pure water as a medium, $D_{max}$ is approximately 1 mm when a voltage is 6 KV. According to the electrode assembly 30 of the present disclosure, since $D_1$ is constant, the total discharge gap increases correspondingly as $D_2$ increases, such that the intensity of shock waves generated at the second discharge point can be enhanced. In one exemplary embodiment of the present disclosure, the length of $D_2$ is greater than the length of $D_1$, so that more energy are applied on the calcification lesion portion. In one exemplary embodiment of the present disclosure, $D_2$ can be appropriately adjusted in advance according to the degree of calcification of a cardiac valve or a blood vessel of a treatment subject. In another exemplary embodiment of the present disclosure, $D_2$ can be adjusted according to actual needs during a surgery to achieve an optimal therapeutic effect. For example, it is possible to make $D_2$ decrease to be smaller than $D_1$ during pre-dilation, so that energy is concentrated at the first discharge point; and after the balloon enters into a valvular annulus, it is possible to increase $D_2$ to be greater than $D_1$ ($D_2>D_1$), so that more energy is concentrated at the second discharge point. The specific method for adjusting $D_2$ is not specifically limited. For example, the outer electrode 304 may be connected to a control apparatus at a handle of the shock wave apparatus as shown in FIG. 2 by means of an insulating guide wire (not shown in the figures), such that the outer electrode 304 can be moved by means of the guide wire and the control apparatus, so as to adjust $D_2$. In one exemplary embodiment of the present disclosure, $D_2$ is 0.2 mm to 0.9 mm, and preferably 0.2 mm to 0.5 mm.

Figure 6A:
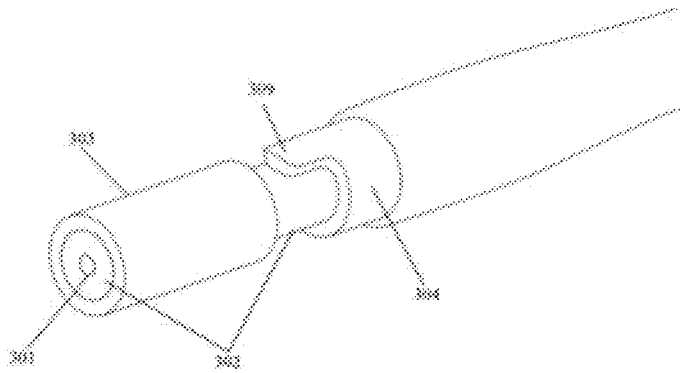
FIGS. 6A and 6B are schematic diagrams of a modified embodiment of the electrode assembly for a shock wave apparatus of the present disclosure.

In one exemplary embodiment of the present disclosure, the outer electrode 304 and/or the first electrical conductor 303 may be provided with a protruding part 309. As shown in FIG. 6A, the protruding part 309 of the outer electrode 304 extends from the terminal end of the outer electrode 304 towards the first electrical conductor 303 along the outer surface of the insulating layer 302, but is not contact to the first electrical conductor 303. In another exemplary embodiment of the present disclosure, the first electrical conductor 303 may be provided with a protruding part 309 (not shown in the figures), which extends from the base end of the first electrical conductor 303 towards the outer electrode 304 along the outer surface of the insulating layer 302, but is not contact to the outer electrode 304. In still another embodiment of the present disclosure, each of the first electrical conductor 303 and the outer electrode 304 may be provided with a protruding part 309. By means of the provision of the protruding part 309, the discharge gap $D_2$ at the second discharge point becomes different in the entire circumferential direction of the electrode assembly 30. Specifically, $D_2$ becomes smaller at a position where the protruding part 309 is provided, and therefore, discharge also occurs between the protruding part 309 and the corresponding first electrical conductor 303/outer electrode 304, instead of randomly occurring across the entire second discharge point. According to the electrode assembly 30 of the described structure, the release and conduction directions of shock wave can be controlled, so as to better cooperate with the shock wave apparatus of the present disclosure that is provided with a plurality of balloons and to realize directed release of a shock wave, thereby further improving the quality and effect. The shape of the protruding part 309 is not specifically limited.

In one embodiment of the present disclosure, when the shock wave apparatus which is provided with the plurality of balloons is used, preferably, each balloon 10 is internally disposed with at least one electrode assembly 30. More preferably, the electrode assembly 30 in each balloon is provided with one protruding part 309. Still more preferably, the protruding part of each electrode assembly 30 is disposed at a side of the second discharge point that faces a position where the shock wave apparatus is in contact with the calcification lesion portion.

In one embodiment of the present disclosure, the inner electrode 301 can be moved inside the insulating layer 302 in the axial direction of the insulating layer 302. For example, the inner electrode 301 may be connected to the control apparatus at the handle (not shown in the figures) of the shock wave apparatus through an insulating guide wire (not shown in the figures), such that the inner electrode 301 can be moved by means of the guide wire and the control apparatus.

Figure 6B:
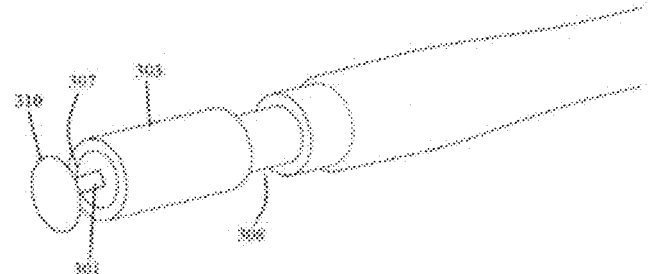

In one embodiment of the present disclosure, the terminal end of the movable inner electrode 301 is provided with the connecting part 310, as shown in FIG. 6B. Preferably, the connecting part 310 can come into contact with the terminal end of the first electrical conductor 303 during the movement of the inner electrode 301, such that the inner electrode 301 is electrically connected to the first electrical conductor 303. According to the electrode assembly 30 of the described structure, when pre-dilation is completed and the balloon enters into the valvular annulus, the tip end (the first discharge point) of the electrode assembly 30 no longer needs to discharge. At this time, the discharge at the first discharge point is cancelled by means of the above-described electrical connection between the inner electrode 301 and the first electrical conductor 303, and discharge only occurs at the second discharge point. Therefore, the calcification lesion portion of the cardiac valve can be treated more effectively. The shape of the connecting part 310 is not specifically defined, as long as it realizes the above-described electrical connection between the inner electrode 301 and the first electrical conductor 303.

Figure 7A:
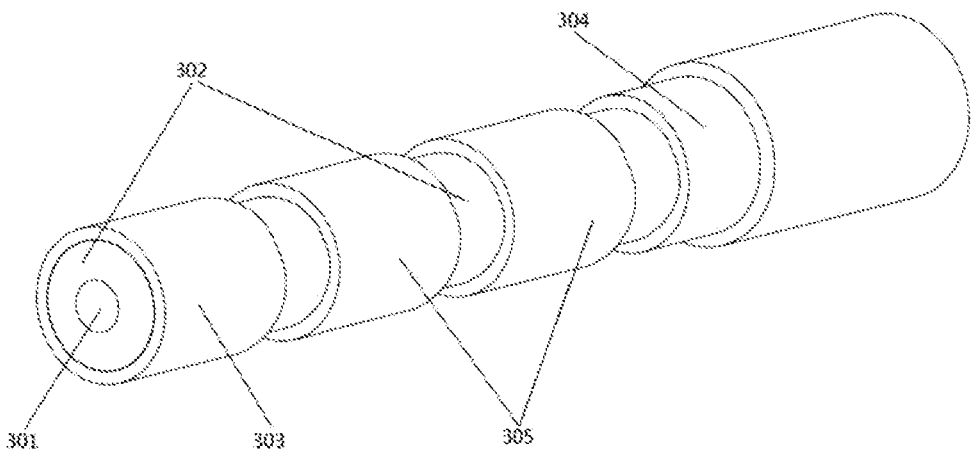
FIGS. 7A and 7B are schematic diagrams of a circuit control system in the modified exemplary embodiment of the electrode assembly for a shock wave apparatus of the present disclosure.

In one embodiment of the present disclosure, in addition to the first electrical conductor 303, the electrode assembly 30 may further be provided with at least one second electrical conductor 305, as shown in FIG. 7A. The second electrical conductor 305 is disposed between the first electrical conductor 303 and the outer electrode 304. When more than two second electrical conductors 305 are provided, the second electrical conductors 305 are arranged at intervals between the first electrical conductor 303 and the outer electrode 304.

The first electrical conductor 303 and the second electrical conductors 305 (hereinafter sometimes collectively referred to as the electrical conductor) are not electrically connected to the power supply unit, and therefore do not have any polarity. The material for forming the second electrical conductor 305 is not specifically limited, may be any conductor, and preferably is metal materials such as stainless steel, copper, etc. The shape of the second electrical conductor 305 is not specifically limited, and the respective shapes of the first electrical conductor 303 and the second electrical conductors 305 may be the same or different.

However, preferably, the second electrical conductors 305 have a shape of annular shape that covers a portion of the outer peripheral surface of the insulating layer 302, as shown in FIG. 7A. The wall thickness of each of the annular second electrical conductors is 0.1 mm to 1.0 mm. The number of second electrical conductors 305 in the electrode assembly 30 is not limited. However, preferably, the electrode assembly 30 is provided with one to four second electrical conductors 305, and more preferably one to two of same.

As shown in FIG. 7A, an insulating gap is provided between the first electrical conductor 303 and the second electrical conductor 305 adjacent thereto, an insulating gap is provided between the outer electrode 304 and the second electrical conductor 305 adjacent thereto, and an insulating gap is provided between any two adjacent second electrical conductors 305.

Figure 7B:
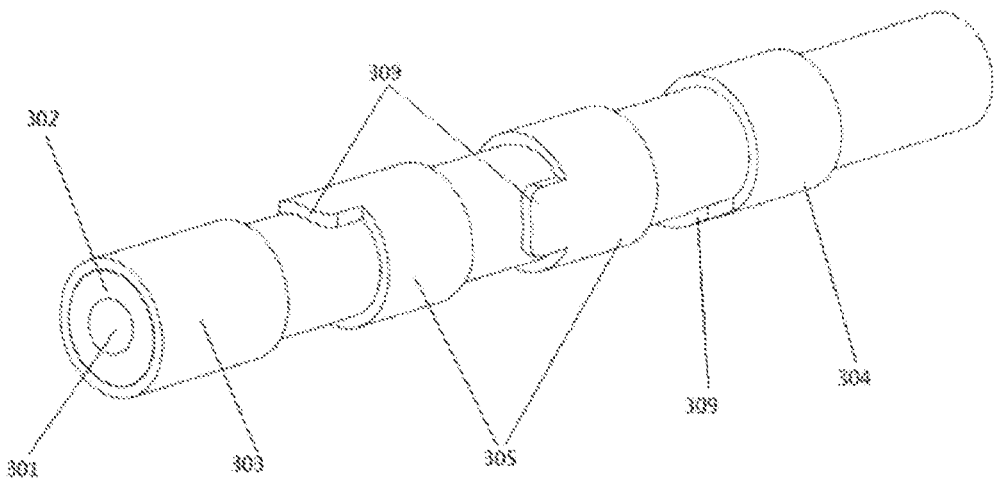

In one exemplary embodiment of the present disclosure, at least one second electrical conductor 30 may be provided with the protruding part 309, as shown in FIG. 7B. The arrangement of the protruding part 309 of the second electrical conductor 305 is similar to the protruding parts of the first electrical conductor 303 and the outer electrode 304, that is, the protruding part 309 extends from an end of the second electrical conductor 305 to the base end or the terminal end of the insulating layer 302 along the outer peripheral surface of the insulating layer 302, but is not in contact with the first electrical conductor 303/second electrical conductor 305/outer electrode 304 adjacent thereto.

According to the electrode assembly 30 of the present disclosure, when a treatment subject having severe cardiac valve and blood vessel calcification, and in particular severe cardiac valve calcification is treated, the balloon of the shock wave apparatus can easily enter into the valvular annulus by means of pre-dilation; moreover, after the balloon enters into the valvular annulus, the discharge of the head end of the electrode assembly 30 may be cancelled, such that energy is concentrated on the treatment of the calcification lesion portion.

Some other exemplary embodiments of the present disclosure will be described below with reference to FIG. 8 to FIG. 12, and for the same or similar components to those of the foregoing exemplary embodiments, details are not described hereinafter again, and differences therebetween are emphasized.

Figure 8:
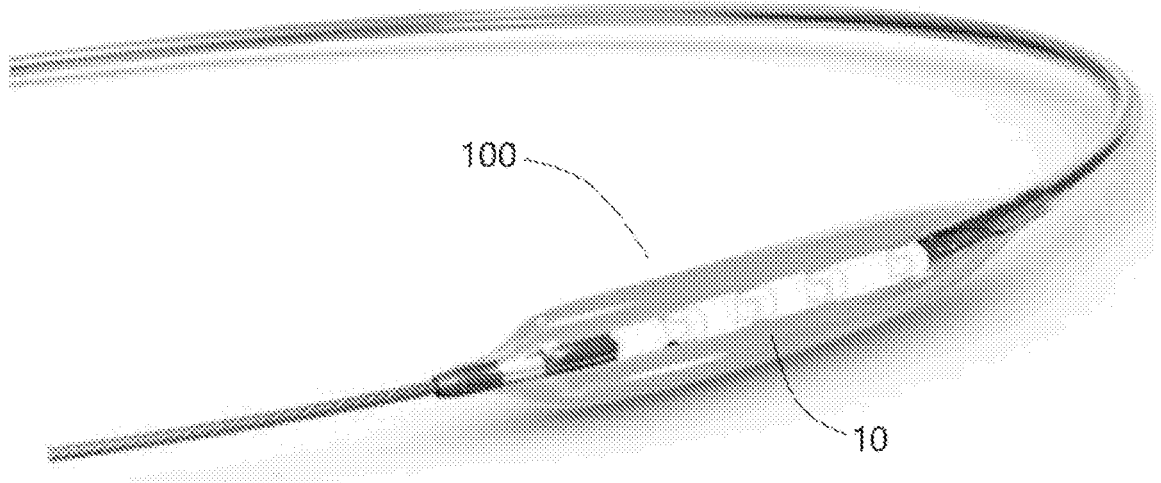
FIG. 8 shows the structure of another exemplary embodiment of a shock wave apparatus of the present disclosure.
Figure 9:
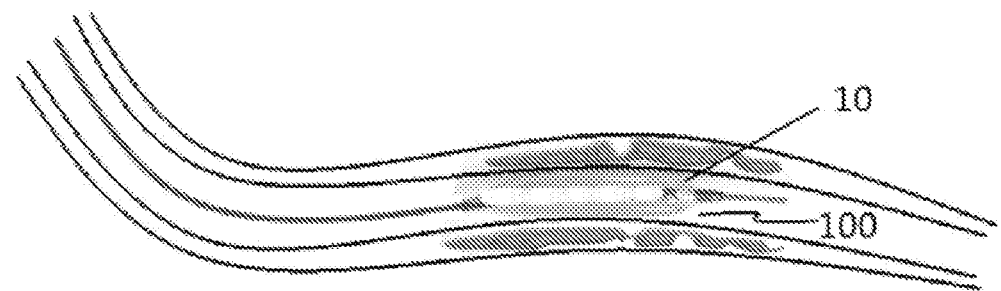
FIG. 9 shows the usage state of another exemplary embodiment of the shock wave apparatus of the present disclosure.

In another exemplary embodiment of the present disclosure, as shown in FIG. 8 and FIG. 9, the shock wave apparatus 100 comprises at least one balloon 10. The balloon 10 is provided with balloon body. Preferably, the balloon body of the balloon 10 is cylindrical after dilated. The shapes of two end parts of the balloon 10 in a lengthwise direction are not specifically defined, as long as the balloon body of the balloon 10 has a shape of cylindrical after being dilated. The balloon 10 of the shock wave apparatus of the present disclosure may also have other shapes.

The balloon 10 is internally disposed with at least one shock wave transmitter which is used for receiving a voltage/current pulse and generating shock wave. The shock wave transmitter comprises at least one electrode cable which receives and conducts a voltage/current pulse and at least one electrode assembly 40 which is electrically connected to the electrode cable and is used for receiving the voltage/current pulse to generate shock wave. The shock wave generated by the electrode assembly 40 is radially conducted to a surface of the balloon 10 through the liquid inside the balloon and is then conducted to the calcification lesion portion through the surface of the balloon.

As shown in FIG. 9, during a surgery, the balloon 10 of the shock wave apparatus 100 is positioned at, for example, a blood vessel. Preferably, the position of the electrode assembly 40 inside the balloon 10 corresponds to the calcification lesion portion, such that the distance between the electrode assembly 40 and the calcification lesion portion is the shortest.

Figure 10A:
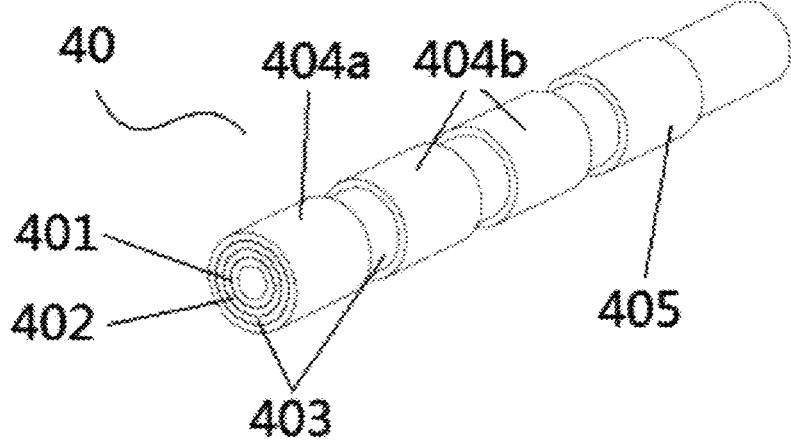
FIG. 10A-FIG. 10C are schematic diagrams of an exemplary embodiment of an electrode assembly for a shock wave apparatus of the present disclosure.

As is shown in FIG. 10A, the electrode assembly 40 comprises an inner insulating layer 401, an inner electrode 402, an outer insulating layer 403, a first electrical conductor 404a and an outer electrode 405.

Figure 10B:
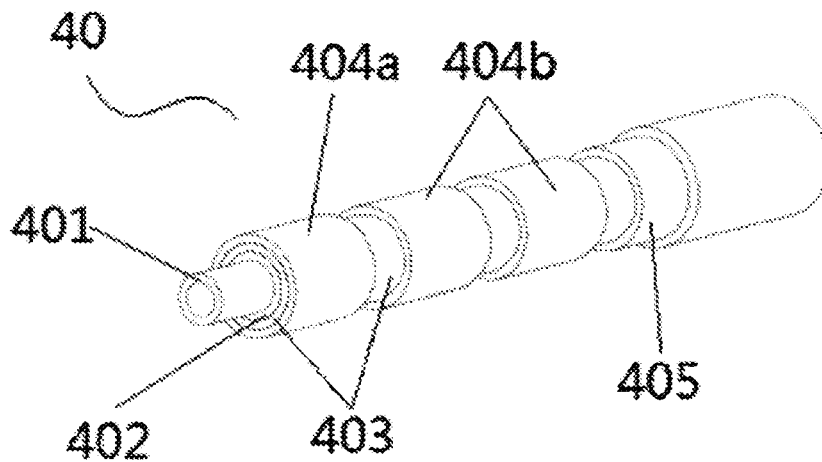
Figure 10C:
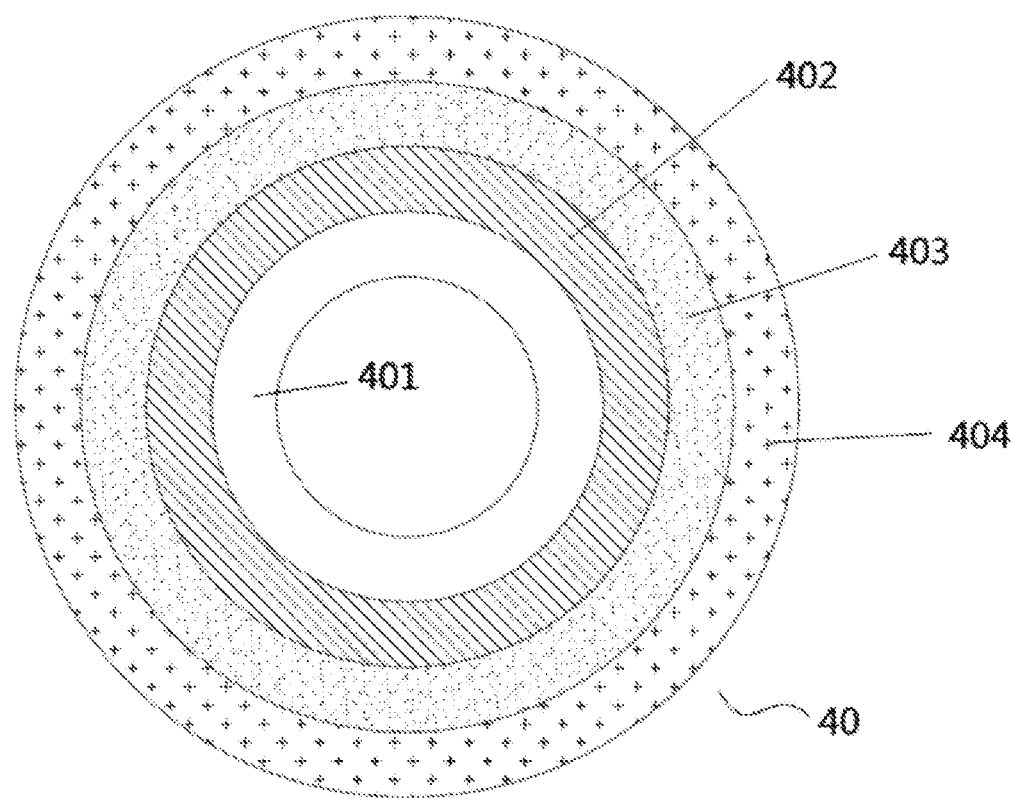

The inner insulating layer 401 functions as a second insulating layer which is located on the innermost side of the electrode assembly 40, as shown in FIG. 10A. Preferably, the inner insulating layer 401 is an elongated hollow insulator made of an insulating material. The inner insulating layer 401 may be used as a guide cavity so that guide wire(s) or other components of the shock wave apparatus pass through an inner cavity of the inner insulating layer 401. When being used as, for example, the guide cavity, the inner insulating layer 401 may protrude with respect to the other components of the electrode assembly 40, as shown in FIG. 10B. Moreover, when being used as the guide cavity, the inner insulating layer 401 and the balloon 10 are in sealed connection at both ends of the balloon 10. The material for forming the inner insulating layer 401 is not specifically limited, but is preferably a high-voltage resistant material such as polyimide or polytetrafluoroethylene. The shape of an outer insulating layer 403 is not specifically limited, but an insulating sheath with an annular cross section is preferred, as shown in FIG. 10C. The inner diameter of the inner insulating layer 401 shaped into an annular insulating sheath is 0.3 mm to 0.4 mm, and preferably 0.3 mm to mm. The wall thickness of the inner insulating layer 401 is preferably 0.1 mm to 0.2 mm, and more preferably 0.1 mm to 0.15 mm.

When the guide wire(s) or other components of the shock wave apparatus are not required to pass through inside of the inner insulating layer 401, the electrode assembly 40 of the present disclosure may be provided with no inner insulating layer 401.

As shown in FIG. 10A, an inner electrode 402 is disposed on an outer side of the inner insulating layer 401 and covers at least a portion of an outer peripheral surface of a terminal end of the inner insulating layer 401. A terminal end of the inner electrode 402 is exposed from a terminal end of the outer insulating layer (i.e., a first insulating layer) 403. The terminal end of the inner electrode 402 may be aligned with the terminal end of the outer insulating layer 403, or alternatively, the terminal end of the inner electrode 402 may protrude from the terminal end of the outer insulating layer 403. The inner electrode 402 is electrically connected to a power supply unit by means of one wire of an electrode cable. The material for forming the inner electrode 402 is not specifically limited, may be any electrical conductor, but is preferably a metal material such as copper, silver, tungsten, etc. The shape of the inner electrode 402 is not specifically limited, but, as shown in FIG. 10C, the inner electrode 402 is preferably an annular electrode with a circular cross section. The wall thickness of the annular inner electrode 402 is 0.05 mm to 0.2 mm, and preferably 0.1 mm to 0.15 mm.

The outer insulating layer 403 is the first insulating layer and has an elongated hollow structure. Both the inner insulating layer 401 and the inner electrode 402 are located in an interior space of the outer insulating layer 403. Specifically, as shown in FIG. 10A, the inner electrode 402 is disposed in a gap between the inner insulating layer 401 and the outer insulating layer 402. A terminal end of the inner electrode 402 is exposed from the terminal end of the outer insulating layer 403. The terminal end of the inner electrode 402 may be aligned with the terminal end of the outer insulating layer 403, or alternatively, the terminal end of the inner electrode 402 may protrude from the terminal end of the outer insulating layer 403.

The material for forming the outer insulating layer 403 is not specifically limited, and may be any insulator, but is preferably high-voltage resistant material such as polyimide or polytetrafluoroethylene. The shape of the outer insulating layer 403 is not specifically limited, but an insulating sheath with an annular cross section is preferred, as shown in FIG. 10C. The wall thickness of the outer insulating layer shaped into the insulating sheath is 0.1 mm to 0.2 mm, and preferably mm to 0.15 mm. A length of the inner electrode 402 being exposed from a distal end of the outer insulating layer 403 is not specifically limited.

A first electrical conductor 404a is disposed on at least a portion of an outer peripheral surface of the terminal end of the outer insulating layer 403. A terminal end of the first electrical conductor 404a may be aligned with the terminal end of the outer insulating layer 403, or alternatively, the terminal end of the first electrical conductor 404a may protrude from the terminal end of the outer insulating layer 403. However, preferably, the terminal end of the first electrical conductor 404a is aligned with the terminal end of the outer insulating layer 403.

In one exemplary embodiment of the present disclosure, in addition to the first electrical conductor 404a, the electrode assembly 40 is further provided with at least one second electrical conductor 404b. As shown in FIG. 10B, the first electrical conductor 404a is disposed on the outer peripheral surface of the terminal end of the outer insulating layer 403, and the second electrical conductors 404b are sequentially arranged at intervals along a direction directed to the base end of the outer insulating layer 403.

None of the first electrical conductor 404a and the second electrical conductors 404b (hereinafter, collectively referred to as electrical conductors 404 sometimes) is electrically connected to the power supply unit, and therefore none of electrical conductor 404 has any polarity. The material for forming the electrical conductors 404 is not specifically limited, may be any electrical conductor, but is preferably a metal material such as stainless steel, copper, etc. The shape of the electrical conductor 404 is not specifically limited, and the respective shapes of the first electrical conductor 404a and the second electrical conductor 404b may be the same as or different from each other. However, preferably, an annular shape that covers a portion of the outer peripheral surface of the outer insulating layer 403 is preferred, as shown in FIG. 10C. The wall thickness of each of the annular electrical conductors 404 is 0.1 mm to 0.2 mm, and preferably 0.1 mm to 0.15 mm. The specific number of second electrical conductors 404b in the electrode assembly 40 is not limited. However, preferably, the electrode assembly 40 is provided with one to five second electrical conductors 404b, and more preferably two to three of second electrical conductors 404b.

As shown in FIG. 10A and FIG. 10B, compared to the electrical conductors 404, an outer electrode 405 is disposed at the base end of the outer insulating layer 403 and covers a portion of the outer peripheral surface of the outer insulating layer 403. The outer electrode 405 is electrically connected to the power supply unit by means of one wire of the electrode cable. The material forming the outer electrode 405 is not specifically limited, but is preferably a metal material such as stainless steel, copper, etc. The shape of the outer electrode 405 is not specifically limited, but is preferably an annular shape that covers the outer peripheral of the base end of the outer insulating layer 403, as shown in FIG. 10C. The wall thickness of the annular outer electrode 405 is 0.05 mm to 0.2 mm, and preferably 0.1 mm to 0.15 mm.

As shown in FIG. 10A, an insulating gap is provided between the first electrical conductor 404a and the outer electrode 405, which are disposed on the outer peripheral surface of the outer insulating layer 403. Moreover, as shown in FIG. 10B, an insulating gap is provided between the first electrical conductor 404a and the second electrical conductor 404b adjacent thereto, between the outer electrode 405 and the second electrical conductor 404b adjacent thereto, and between any two adjacent second electrical conductors 404b.

In an electrode assembly 40 as shown in FIG. 10A, a discharge principle thereof is basically the same as that of the above-described electrode assembly 30. Specifically, according to voltage dividing principle in series circuits, there are voltage differences at a gap between the terminal end of the inner electrode 402 and a first electrical conductor 404a (a first discharge point), a gap between the first electrical conductor 404a and the second electrical conductor 404b adjacent thereto, a gap between any two adjacent second electrical conductors 404b of the plurality of second electrical conductors 404b and a gap between the second electrical conductor 404b adjacent to the outer electrode 405 and the outer electrode 405 (a plurality of second discharge points). Mediums at the first discharge point and the plurality of second discharge points are broken down at the same time and shock wave energy is generated due to the presence of above voltage differences.

According to the above electrode assembly 40, discharge can be realized at multiple points at the same time. Therefore, compared to a single-point discharge electrode assembly in the prior art, as for the treatment of a treatment subject having blood vessel calcification, and in particular severe coronary vessel calcification which making it difficult for a balloon to enter into a calcification lesion portion, preliminary treatment can be performed on the calcification lesion portion at first by means of discharge of the head end of the electrode assembly 40, such that the calcification lesion portion turns into soft. That is, a pre-dilation function on a vessel with severe calcification can be achieved by the discharge of the head end of the electrode assembly 40, making it easy for the balloon 10 of the shock wave apparatus to enter into the calcification lesion portion smoothly. Shock waves generated at the second discharge points can further act on the calcification lesion portion after the balloon 10 smoothly enters into the calcification lesion portion. Therefore, more satisfactory effects can be obtained when the electrode assembly 40 of the present disclosure is used to treat a treatment subject having, for example, severe coronary vessel calcification.

For the setting of a discharge gap, etc. in the electrode assembly 40 shown in FIG. 10A to FIG. 10C, reference can be made to the above-described electrode assembly 30.

Figure 11:
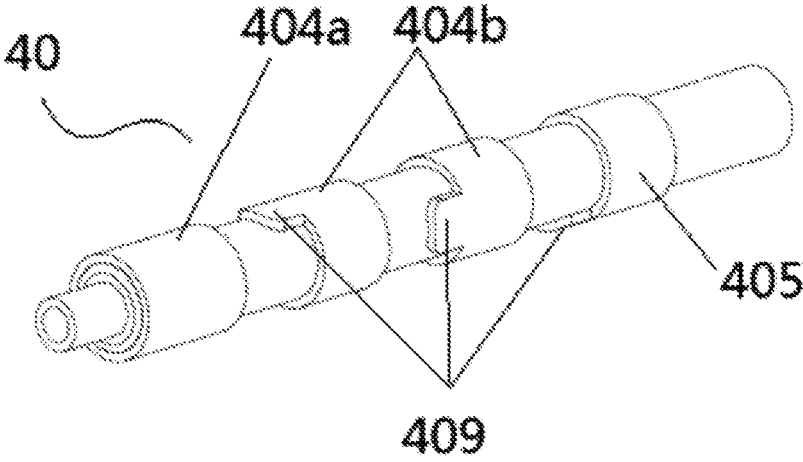
FIG. 11 is a schematic diagram of a modified embodiment of the electrode assembly for a shock wave apparatus of the present disclosure.

As shown in FIG. 11, in an exemplary embodiment of the present disclosure, the outer electrode 405 and/or the first electrical conductor 404a may be provided with a protruding part 409, similarly to the electrode assembly 30. In addition, any of one or more of the plurality of second electrical conductors 404b may be provided with a protruding part 409. The protruding parts 409 of the second electrical conductors 404b are disposed in a similar manner to the protruding parts of the first electrical conductor 404a and the outer electrode 405, that is, extending from one end of the second electrical conductor 404b to the base end or terminal end of the outer insulating layer 403 along the outer peripheral surface of the outer insulating layer 403, but being not contact with the adjacent first electrical conductor 404a/second electrical conductor 404b/outer electrode 405.

By means of the provision of the protruding parts 409, the discharge gap $D_2$ at the second discharge point 408 becomes different in the entire circumferential direction of the electrode assembly 40. Specifically, $D_2$ becomes smaller at a position where the protruding part 409 is provided, and therefore, discharge also occurs between the protruding part 409 and the corresponding first electrical conductor 404a/outer electrode 405, instead of randomly occurring across the entire second discharge point 408. According to the electrode assembly 40 of the described structure, the release and conduction directions of shock waves can be controlled, and it realizes directed release of shock waves, thereby further improving the quality and effects. The shape of the protruding part 409 is not specifically limited.

The numbers of respective protruding parts of the outer electrode 405 and the plurality of electrical conductors 404, and total number of protruding parts provided on the outer electrode 405 and the plurality of electrical conductors 404 are not specifically limited. However, preferably, any one of the outer electrode 405 and the plurality of electrical conductors 404 is only provided with one protruding part 409. When the outer electrode 405 and the plurality of electrical conductors 404 are provided with more than two protruding parts in total, the more than two protruding parts 409 are uniformly distributed on the circumference of the cross section of the electrode assembly 40. That is, when there are N protruding parts 409 in total, the two or more protruding parts are spaced apart from one another on the circumference of the cross section of the electrode assembly 40 by an angle of $\alpha$, and $\alpha=360°/N$. Specifically, when N is 2, $\alpha$ is 180°; when N is 3, $\alpha$ is 210°; and so on. The extension directions of the protruding parts 409 on the outer electrode 405 and the plurality of electrical conductors 404 are not specifically limited. However, preferably, each second discharge point is only provided with one protruding part.

Figure 12A:
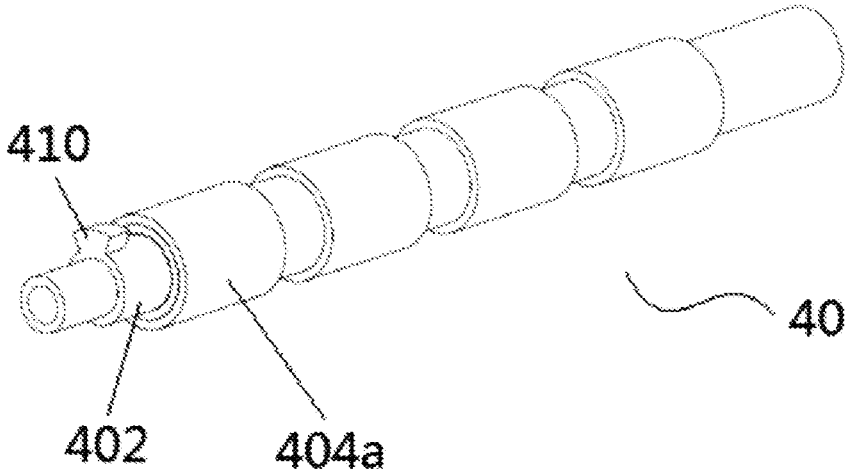
FIG. 12A and FIG. 12B are schematic diagrams of a modified embodiment of the electrode assembly for a shock wave apparatus of the present disclosure.
Figure 12B:
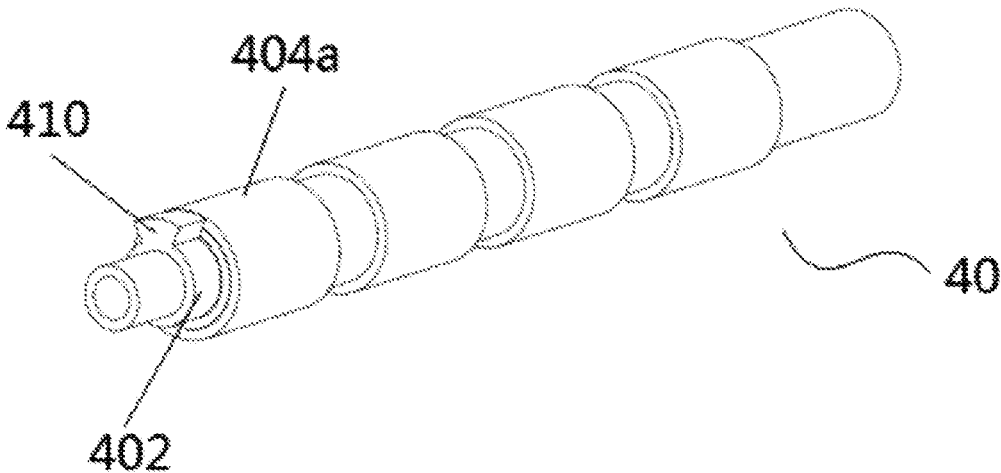

As is shown is FIG. 12, in an exemplary embodiment of the present disclosure, the terminal end of the inner electrode 402 is provided with the connecting part 410. Preferably, the connecting part 410 can come into contact with the terminal end of the first electrical conductor 404a during the movement of the inner electrode 402, such that the inner electrode 402 is electrically connected to the first electrical conductor 404a. The connection part 410 can make a similar effects and functions as those of the above-described connection part 310, at the calcification lesion portions of blood vessels.

According to the electrode assembly 40 of the present invention, when a treatment subject having severe blood vessel calcification, and in particular severe blood vessel wall calcification is treated, the balloon of the shock wave apparatus can easily enter into the calcification lesion portion by means of pre-dilation; moreover, the discharge of the head end of the electrode assembly 40 may be cancelled after the balloon enters into the calcification lesion portion, such that energy is concentrated on the treatment of the calcification lesion portion.

Figure 13:
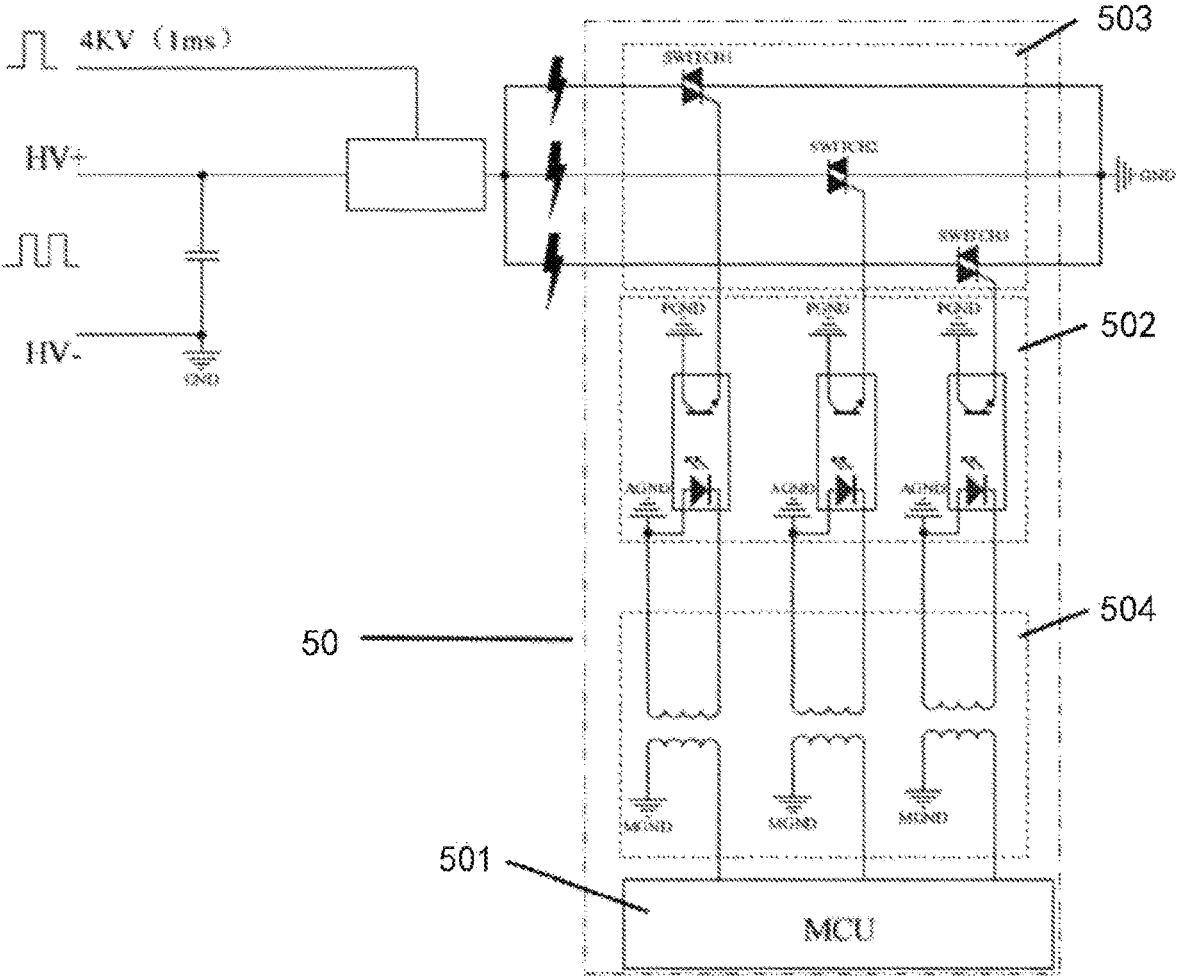
FIG. 13 is a schematic diagram of a circuit control system of the shock wave apparatus of the present disclosure.

In one exemplary embodiment of the present disclosure, the shock wave apparatus 100 comprises a circuit control system 40 for controlling the shock wave transmitter 20. As shown in a dashed line box in FIG. 13, the circuit control system 50 of the shock wave apparatus of the present disclosure comprises a control unit 501, a high-voltage isolation unit 502 and a multi-channel control unit 503.

The control unit 501 is delayed by single chip microcomputer program software or controlled by a hardware timer circuit, and a plurality of output pins respectively correspond to multiple electrodes, so as to transmit a low-level signal, a high-level signal or a PWM signal, thereby realizing the control over a switch component in the multi-channel control unit 503.

The high-voltage isolation unit 502 is also referred to as a high-voltage isolation circuit. An electrode has an operation voltage of 1 KV to 20 KV when discharging, and thus generates a strong a peak voltage/current and electromagnetic interference during the discharge. However, the control unit 501 only has an operation voltage of 3 V to 5 V, and is poor in resistance to interference. In addition, a high-voltage switch device needs a larger driving voltage/current, and cannot be directly driven by a signal which is outputted by a single chip microcomputer, and thus it is necessary to boost a driving signal before performing control. The high-voltage isolation circuit 503 may use devices such as an optocoupler to enhance a driving capacity of an output signal of the single chip microcomputer of the control unit, while ensuring effective isolation between the control circuit and a load circuit, isolating a digital signal from an analog signal, and avoiding the high-voltage load circuit from interfering with the control circuit.

The multi-channel control unit 503 is also referred to as a multi-channel separate control switch, which is used for controlling the switching on and off of a circuit. Specific examples of the multi-channel separate control switch include, but not limited to high-voltage switch devices such as a high-voltage relay, a high-voltage thyristor and a high-voltage IGBT. When the control unit 501 outputs a low-level signal, the switch is switched off; when the control unit 501 outputs a high-level signal, the switch is switched on; and when the control unit 501 outputs a PWM signal, the switch is periodically switched on and off. In the multi-channel control unit of the present disclosure, components need a larger parameter of withstand voltage and an over-current capacity greater than 20 A, and dv/dt should be greater than 7000 V/μs, so as to ensure the stability of switch performance. A high-voltage trigger switch is controlled by means of the multi-channel control unit 503, such that the discharge of the electrode assembly 30 is enabled by means of a high-voltage energy storage capacitor.

In one exemplary embodiment of the present disclosure, the circuit control system may also include a low-voltage isolation unit 504. The low-voltage isolation unit 504 is also referred to as a low-voltage isolation circuit, and specific examples thereof include a digital isolator, etc., which can satisfy an electrical safety standard or reduce noise of a grounding loop, etc. By means of the low-voltage isolation unit 504, dual-isolation between a digital signal and an analog signal can be realized, a carrying capacity of the control signal is improved, and it reduces or avoids influence of multiple optical isolation components on the speed and power consumption.

According to the circuit control system of the present disclosure in the exemplary embodiment, multi-channel control can be realized only by means of one boost circuit, and thus the overall volume of a high-voltage generator can be reduced by more than ten times, and a control circuit board can be realized only by means of a PCB with an area of 10 cm*10 cm.

In one exemplary embodiment of the present disclosure, shock wave transmitters 20 in a plurality of balloons 10 may be respectively controlled during a surgery according to the actual condition of a treatment subject, so as to respectively generate shock waves of different intensities. The degrees of dilation of the plurality of balloons 10 may also be respectively controlled, such that the intensities of shock waves that are transmitted to calcification lesion portions having different degrees of calcification are respectively controlled. The above two methods may also be combined, generating/transmitting shock waves of different intensities for the calcification lesion portions having different degrees of calcification.

The structure and use of the shock wave apparatus of the present disclosure are described by taking human as a treatment subject in the exemplary embodiments of the present disclosure. However, the treatment subject of the shock wave apparatus of the present disclosure is not limited to human, but may also be other animals. For example, an object of the patent for the shock wave apparatus of the present disclosure may be pets such as cats and dogs, may also be large animals such as cattle and horses, and may also be rare wild animals such as pandas.

The foregoing are merely exemplary embodiments of the present disclosure, but are not intended to limit the patent scope of the present disclosure. Any transformation of equivalent structures or equivalent procedures made using the description and accompanying drawings of the present disclosure, which is directly or indirectly applied in other relevant technical fields, should similarly fall within the scope of patent protection of the present disclosure.

What is claimed is:

1. An electrode assembly for a shock wave apparatus, the electrode assembly configured to be disposed inside a balloon of the shock wave apparatus, and characterized in comprising:

a first electrode;

an insulating layer, the first electrode being disposed inside the insulating layer and a terminal end of the first electrode being exposed from a terminal end of the insulating layer;

a first electrical conductor disposed on at least a portion of an outer peripheral surface of the terminal end of the insulating layer, so as to form a first discharge point between the terminal end of the first electrode and the first electrical conductor where a shock wave is generated forwardly in an axial direction of the electrode assembly; and a second electrode disposed on at least a portion of an outer peripheral surface of a base end of the insulating layer, such that an insulating gap is provided between the second electrode and the first electrical conductor, wherein the first electrode can be moved inside the insulating layer in an axial direction, and wherein the terminal end of the first electrode is provided with a connecting part, which is configured to contact with a terminal end of the first electrical conductor when a discharge at the first discharge point is no longer needed.

2. The electrode assembly according to claim 1, characterized in that at least one of the first electrical conductor and the second electrode is provided with a protruding part which extends from one of the first electrical conductor and the second electrode toward the other of the first electrical conductor and the second electrode along an outer peripheral surface of the insulating layer.

3. The electrode assembly according to claim 1, characterized in that the electrode assembly further comprises at least one second electrical conductor which is disposed on at least a portion of the outer peripheral surface of the insulating layer and is located between the first electrical conductor and the second electrode, such that an insulating gap is provided between the first electrical conductor and the at least one second electrical conductor and between the at least one second electrical conductor and the second electrode.

4. The electrode assembly according to claim 3, characterized in that the at least one second electrical conductor is provided with a protruding part which extends from the at least one second electrical conductor toward the base end or the terminal end of the insulating layer along the outer peripheral surface of the insulating layer.

5. The electrode assembly according to claim 3, characterized in that the first electrical conductor, the at least one second electrical conductor and the second electrode are provided with two or more protruding parts in total, the two or more protruding parts are spaced apart from one another in a circumferential direction of the insulating layer by an angle of $\alpha$, $\alpha=360°/N$, and N is the number of the protruding parts.

6. The electrode assembly according to claim 3, characterized in that each of the first electrical conductor and the at least one second electrical conductor is an annular electrical conductor having a wall thickness of 0.1 mm to 1.0 mm.

7. The electrode assembly according to claim 1, characterized in that the first electrode is a rod-shaped electrode having a diameter of 0.1 mm to 1.0 mm.

8. The electrode assembly according to claim 1, characterized in that the second electrode is an annular electrode having a wall thickness of 0.1 mm to 1.0 mm.

9. The electrode assembly according to claim 1, characterized in that the insulating layer is a cylindrical insulating sheath having a wall thickness of 0.1 mm to 1.0 mm.

10. The electrode assembly according to claim 1, characterized in further comprising a second insulating layer, the second insulating layer being disposed inside the insulating layer, and the first electrode being disposed on at least a portion of an outer peripheral surface of a terminal end of the second insulating layer.

11. The electrode assembly according to claim 10, characterized in that the electrode assembly comprises two or more second electrical conductors with an insulating gap provided between any two adjacent second electrical conductors.

12. The electrode assembly according to claim 10, characterized in that the electrode assembly comprises two to five second electrical conductors.

13. The electrode assembly according to claim 10, characterized in that the first electrode is an annular electrode having a wall thickness of 0.05 mm to 0.2 mm, and the second electrode is an annular electrode having a wall thickness of 0.05 mm to 0.2 mm.

14. The electrode assembly according to claim 10, characterized in that the first electrical conductor is an annular electrical conductor having a wall thickness of 0.05 mm to 0.2 mm.

15. The electrode assembly according to claim 10, characterized in that the second insulating layer is a cylindrical insulating layer having an inner diameter of 0.3 mm to 0.4 mm and a wall thickness of 0.1 mm to 0.2 mm.

16. A shock wave apparatus, characterized in that the shock wave apparatus comprises two or more balloons, and at least one balloon of the two or more balloons is internally provided with the electrode assembly according to claim 1.

17. A method for treating cardiac valve calcification, the method comprising treating a calcified portion of a cardiac valve with the shock wave apparatus according to claim 16.

\*   \*   \*   \*   \*